(12) United States Patent
Sawrey et al.

(10) Patent No.: US 7,767,863 B2
(45) Date of Patent: Aug. 3, 2010

(54) METHOD TO MAKE METHYL ISOBUTYL KETONE AND DIISOBUTYL KETONE

(76) Inventors: Jeffrey S. Sawrey, 15 Heywood Rd., Westford, MA (US) 01886; Richard W. Wegman, 912 Glendale Ave., South Charleston, WV (US) 25303

( * ) Notice: Subject to any disclaimer, the term of this patent is extended or adjusted under 35 U.S.C. 154(b) by 0 days.

(21) Appl. No.: 11/991,277

(22) PCT Filed: Sep. 26, 2006

(86) PCT No.: PCT/US2006/037266
§ 371 (c)(1),
(2), (4) Date: Aug. 21, 2009

(87) PCT Pub. No.: WO2007/038440
PCT Pub. Date: Apr. 5, 2007

(65) Prior Publication Data
US 2009/0306434 A1 Dec. 10, 2009

Related U.S. Application Data

(60) Provisional application No. 60/720,982, filed on Sep. 27, 2005.

(51) Int. Cl.
C07C 45/67 (2006.01)
C07C 45/70 (2006.01)
C07C 45/73 (2006.01)
(52) U.S. Cl. .................. 568/388; 568/396; 568/403
(58) Field of Classification Search ............. 568/396, 568/388, 403
See application file for complete search history.

(56) References Cited

U.S. PATENT DOCUMENTS

| | | | |
|---|---|---|---|
| 3,379,766 A | 4/1968 | Hwang et al. | |
| 4,704,478 A | 11/1987 | Olson | |
| 5,059,724 A | 10/1991 | Chen et al. | |
| 5,149,881 A | 9/1992 | Ushikubo et al. | |
| 5,684,207 A | 11/1997 | Chen et al. | |
| 5,925,796 A | 7/1999 | Bassett et al. | |
| 6,008,416 A | 12/1999 | Lawson et al. | |
| 6,762,328 B2 | 7/2004 | Saayman et al. | |

FOREIGN PATENT DOCUMENTS

| | | |
|---|---|---|
| EP | 0227868 | 8/1987 |
| GB | 1317304 | 5/1973 |
| JP | 48013086 | 4/1973 |
| WO | 9965851 | 12/1999 |

OTHER PUBLICATIONS

J. Bian, et al., "Reaction Process Preparation Ketone Catalyst", Derwent Abstract, 2001-183683 of CN 1273231.
Showa Denko, "Acetone Methyl Isobutyl Ketone Produce Isopropanol Yield", Derwent Abstract, 1973-24153U of JP 48013086.
T. Maki, et al., "One Step Prepn. of Methyl Ethyl Ketone—by Liq. Phase Reaction of Acetone with Hydrogen in Presence of Mixed Catalyst", Derwent Abstract, 1988-157200 of JP 63096147.
Xiao-Hong Liu, et al., "Preparation of Nanosized Zirconium Dioxide Supported Palladium Catalyst and Research of its Reduction and Condensation Performance", Chemical Abstract, 2004-68948 of Jingxi Huagong Journal.

*Primary Examiner*—Sikarl A Witherspoon

(57) ABSTRACT

An improved method for the manufacture of MIBK and DIBK from DMK and/or IPA, by reacting, in the presence of an aldol condensation catalyst, a gaseous mixture comprising hydrogen and DMK and/or IPA. The improvement is the use of a reaction pressure greater than 207 kPa (30 psig) to increase the ratio of MIBK to DIBK. In addition a method for the manufacture of MIBK and DIBK by reacting, in the presence of an aldol condensation catalyst, a gaseous mixture consisting essentially of DMK and/or IPA and optionally water.

7 Claims, 3 Drawing Sheets

METHOD TO MAKE METHYL ISOBUTYL KETONE AND DIISOBUTYL KETONE

CROSS REFERENCE TO RELATED APPLICATIONS

This application is a 371 of PCT/US06/037266 filed Sep. 26, 2006, which claims the benefit of U.S. Provisional Application Ser. No. 60/720,982, filed Sep. 27, 2005.

This application claims the benefit of priority of U.S. Patent Application 60/720,982 filed Sep. 27, 2005.

BACKGROUND OF THE INVENTION

This invention relates to the production of methyl isobutyl ketone (MIBK) and diisobutyl ketone (DIBK) by the catalytic reaction of acetone (DMK) and/or isopropyl alcohol (IPA). More specifically, this invention relates to a method for altering the ratio of MIBK to DIBK produced by adjusting the reaction pressure.

MIBK and DIBK are important industrial solvents. As discussed in U.S. Pat. No. 5,925,796 (herein fully incorporated by reference) MIBK and DIBK can be co-produced by the catalyzed reaction of hydrogen and DMK and/or IPA. Typically, an aldol condensation catalyst is used. The MIBK to DIBK ratio is not constant and decreases as steps are taken to increase MIBK production by increasing reactant conversion. This phenomenon is illustrated in the FIGURE of the '796 patent, showing an empirically determined, fitted line which depicts the DIBK/MIBK ratio as a function of the MIBK produced. Unfortunately, the needs of the marketplace do not necessarily conform to the natural tendencies of the chemistry. Thus, if it is desired to increase the MIBK production to meet market demands, an excessive amount of DIBK may be produced, resulting in the need to store or destroy some of the DIBK, and to accept the related raw material inefficiencies and energy penalties. Accordingly, it would be very desirable to have a method whereby the DIBK/MIBK ratio is more readily controlled, permitting the manufacturing operation to, in effect, vary the amount of either material desired and also obtain a more desired amount of the other material, thereby "de-coupling" the usual relationship between the production levels of these two products. The '796 patent disclosed one solution to the above-stated problem. The instant invention provides an alternative or additional solution to this problem.

SUMMARY OF THE INVENTION

The instant invention is an improved method for the manufacture of MIBK and DIBK from DMK and/or IPA, by reacting, in the presence of an aldol condensation catalyst, a gaseous mixture comprising hydrogen and DMK and/or IPA. The improvement comprises a reaction pressure which is greater than 207 kPa (30 psig). The use of such a reaction pressure increases the degree of conversion of the DMK and/or IPA to MIBK and DIBK and increases the ratio of MIBK to DIBK produced at any given degree of conversion. In another embodiment, the instant invention is a method for the manufacture of MIBK and DIBK by reacting, in the presence of an aldol condensation catalyst, a gaseous mixture consisting essentially of DMK and/or IPA and optionally water.

DETAILED DESCRIPTION

Figure 1:
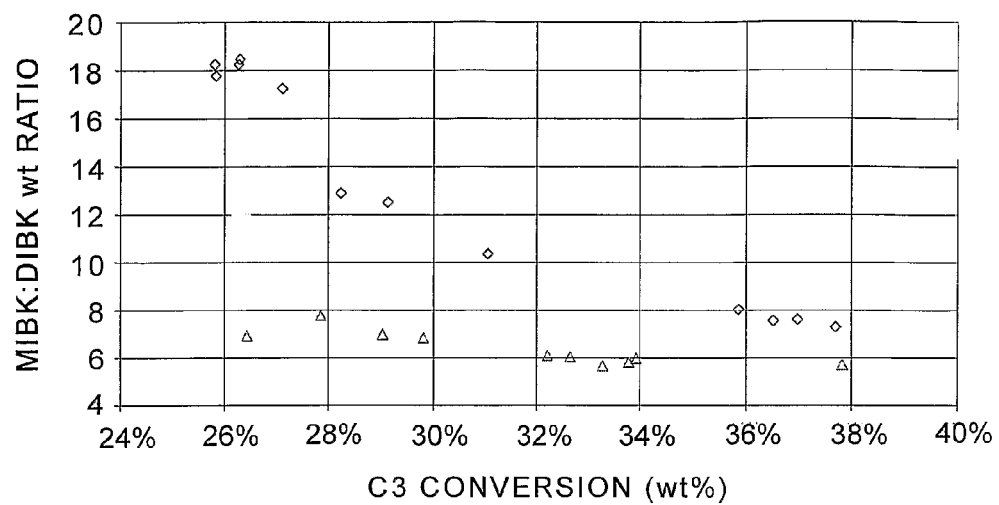
FIGS. 1-5 show data for MIBK-DIBK ratio as a function of conversion as discussed in detail in the EXAMPLES.

Without intending to be bound to any particular chemical theory, it is believed that the co-production of MIBK and DIBK from IPA and/or DMK involves the following reactions:

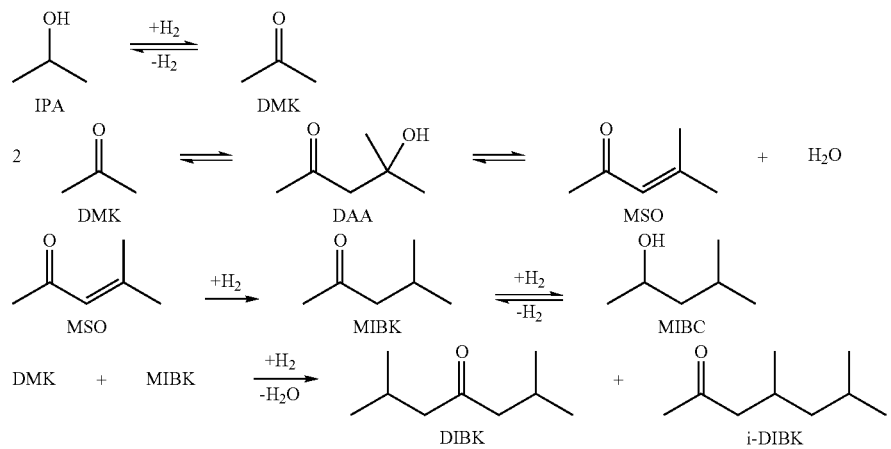

wherein IPA is isopropyl alcohol (isopropanol); DMK is acetone (dimethyl ketone); DAA is diacetone alcohol; MSO is mesityl oxide; MIBK is methylisobutyl ketone; DIBK is diisobutyl ketone; and I-DIBK is iso-DIBK.

It may be noted that isomers of MSO and DIBK exist and can be present in the chemical mix; however, they are not believed to be significant to the instant invention, and are considered herein as normal MSO and DIBK, respectively.

The state of the art upon which the instant invention is an improvement is described in U.S. Pat. No. 5,925,796. As is apparent from the reaction chemistry outlined above, hydrogen is both a product and a reactant in the system. It is preferred that an excess of hydrogen be maintained throughout. This condition is conveniently referred to as the hydrogen balance. As will be recognized by those skilled in the art, the desired hydrogen level can be achieved by such process means as feeding fresh hydrogen, or recycling unused or produced hydrogen from IPA dehydrogenation.

While a multi-functional copper-based catalyst capable of carrying out the condensation/hydrogenation/dehydrogenation/dehydration chemistry is preferably used in the present method, the beneficial effects of the invention are not considered to be dependent on any specific catalyst composition. Accordingly, the present invention should be understood as applicable to any catalyst useful for the production of MIBK and/or DIBK from IPA and/or DMK. Included among such catalysts are those based on the metallic and/or variable oxide states of Group 1-Group 15 elements. Preferably, the multi-functional catalyst will contain one or more metallic and/or variable oxide states of Pd, Ni, Pt, Co, Cu, Cr, Mo, W, Zn, P, As, Sb, Si, Ge, Sn, Al, Ga, Ti, Zr, and Hf, and the alkali and/or alkaline earth metals Li, Na, K, Rb, Cs, Be, Mg, Ca, and Sr. The multi-components of the catalysts, if desired, can be supported on common supports well known in the art such as aluminas, phosphates, silicas, zeolites, clays, and the like. Without being bound to any particular chemical theory, it is believed that alone or in combination the alkali, alkaline earth metals, and/or other metals in their various oxide states, such as Zr, Ti, Al, function as the condensation catalyst and the combination of one or metals such as Pd, Cu, Cr, Ni, in their metallic or various oxide states, function as the hydrogenation/dehydrogenation catalyst. It is also believed that the dehydration step can occur as a thermal reaction or is promoted by one or more of the above mentioned catalyst components and/or supports.

The choice of reaction temperature, within the temperature operating envelope of the chosen catalyst, is not narrowly critical, and can typically range from about 80 to about 300 degrees Celsius depending on catalyst type, preferably from about 180 to about 270 degrees Celsius, more preferably about 200 to about 245 degrees Celsius. Temperatures above about 250 degrees Celsius, depending upon the thermal stability of the specific catalyst in use, are preferably avoided in order to minimize deactivation of the catalyst due to metal sintering. Temperatures below 270 degrees Celsius are often preferred. In the prior art the degree of conversion is in the range of from 20-35% based on temperature, catalyst type and degree of use and typically is 25%. The process of the instant invention increases the conversion by 5% or more.

Surprisingly, the choice of reaction pressure is critical in the instant invention. According to the convention used in the instant invention, all pressures are expressed as gauge pressure. Thus, a pressure of 0 kPa (0 psig) is atmospheric pressure. Surprisingly, it has been discovered that when a reaction pressure greater than 207 kPa (30 psig) is used, then the degree of conversion of the DMK and/or IPA to MIBK and DIBK is increased and the ratio of MIBK to DIBK produced is increased at any given degree of conversion. The maximum pressure of the instant invention is not known but it is believed to be 3450 kPa (500 psig) or greater. Data in the examples below are for a reaction pressure in the range of from 0 kPa (0 psig) to 2070 kPa (300 psig). Preferably, the reaction pressure of the instant invention is in the range of from more than 207 kPa (30 psig) (such as 211 kPa (30.6 psig), 214 kPa (31 psig), 276 kPa (40 psig) or 345 kPa (50 psig)) to 1380 kPa (200 psig). Most preferably, the reaction pressure of the instant invention is in the range of from more than 207 kPa (30 psig) (such as 211 kPa (30.6 psig), 214 kPa (31 psig), 276 kPa (40 psig) or 345 kPa (50 psig)) to 690 kPa (100 psig). However, when the reactants consist essentially of a gaseous mixture DMK and/or IPA and optionally water, then the reaction pressure can be less than 207 kPa (psig) as well as more than 207 kPa (psig).

The catalyst used in the process of the instant invention requires periodic regeneration. The catalyst can typically be regenerated from ten to fifteen times and then is replaced. A freshly regenerated catalyst typically is "hyperactive" for one or two days, producing more DIBK than desired, and then settles down to produce more of the desired MIBK until the catalyst activity drops to a level so low that catalyst regeneration is required. An unexpected benefit of the use of the higher reaction pressure of the instant invention is that a lower reaction temperature can be used while maintaining productivity and that the catalyst has a longer useful life between regenerations thereby significantly increasing the time that the process is producing the higher ratio of MIBK and significantly reducing the cost of catalyst replacement.

The temperature of reaction used in the process of the instant invention is in the broad range described in the prior art '796 patent. However, it has been discovered that when the higher pressure of the instant invention is used, then the ratio of MIBK to DIBK is improved at a somewhat lower reaction temperature (for example, a reduction of reaction temperature from 240 degrees Celsius to a reaction temperature of 210 degrees Celsius) at the same conversion rate.

The flow rate through the reactor is not narrowly critical, and may typically range from about 0.4 to at least about 10.0 LHSV, preferably from about 0.1 to at least about 3.0 LHSV. By the term "LHSV" is meant liquid hourly space velocity, a commonly used measure which equals the volumetric rate of feed in the liquid state per volume of reactor. (As used in the Examples below, it should be pointed out that although the measurement of LHSV is made for the liquid state, the reaction was run in the gas phase and at pressure). Preferably, the flow rate will be in the range of about 0.5 to about 1.5 LHSV, and more preferably in the range of about 0.75 to about 1.25 LHSV.

EXAMPLES

Test Reactor Apparatus

A laboratory reactor is assembled consisting of a 38 cm long, 1.3 cm outside diameter stainless steel U-tube (0.89 mm wall thickness). The reactor is first loaded with catalyst, then 1-2 mm glass beads, and finally a small plug of glass wool to provide containment. The glass beads are used to fill the interstitial spaces of the catalyst bed to maintain maximum vapor velocities and reduce intermolecular mass transfer resistance. Pressure is controlled by a back pressure regulator. Temperature of the reactor is controlled with an electrically heated furnace. The reactor is placed inside an aluminum conduit and the assembly is placed inside the furnace to help keep heat input evenly distributed.

The liquid feed is delivered via a feed pump. The liquid and gas feeds are fully vaporized upon hitting the hot glass beads in the furnace zone. The vapor product leaves the reactor and is condensed in a Friedrich type glass condenser and cooled with either a refrigeration loop or a flow of cold water. The condensed product is collected and analyzed via a HP 6890 gas chromatograph equipped with a DB WAX 30 meter'0.32 mm×0.25 micron capillary column. Water in the product is analyzed via Karl Fischer titration.

Example 1

Preparation of Zirconium/Phosphate—Palladium Catalyst 75.1 g of $ZrOCl_2 \cdot 8H_2O$ is dissolved in 1.8 L of 1N HCl (solution A). 34.8 g of 85% $H_3PO_4$ is added to 1.6 L of distilled $H_2O$ and this mixture is added to solution A over a five minute time period. A white precipitate forms. After the addition is complete the mixture is left stirring for four hours. The stirrer is shut off and the mixture rests for 16 hours. The precipitate is then collected by filtration using a Buchner funnel and Whatman #4 filter paper. A gel is recovered and slurried in 2 L distilled water and filtered as before. This step was repeated until the filtrate pH=4. The gel is allowed to air dry under suction, isolated, and then dried at 110 degrees Celsius for 48 hr. After drying the solid is sieved to 8-10 mesh. 24.4 g of the sieved material is impregnated by incipient wetness with 0.42 g $Pd(NO_3)_2 \cdot xH_2O$ dissolved in 17 ml of deionized water. The resulting zirconium phosphate contains 0.7 wt % Pd, and is dried at 110 degrees Celsius for 24 hr.

Condensation of DMK Using the Zirconium/Phosphate—Palladium Catalyst 20.9 g of the zirconium phosphate catalyst is charged into the reactor. The reactor is heated to 105 degrees Celsius, pressurized to about 620 kPa (90 psig) with $N_2$ and fed with acetone (DMK) at LHSV=1.0 $hr^{-1}$ for 48 hr. The acetone feed is then stopped and the catalyst is reduced at 90 degrees Celsius with a $N_2:H_2=2:1$ gas mixture at 55 ml/min for 3 hr. After the reduction, an acetone:water=97:3 mixture is fed to the reactor at LHSV=1.0 $hr^{-1}$. The $H_2$ flow=38 ml/min. The catalyst bed temperature is varied from 90 to 110 degrees Celsius by controlling the temperature of the furnace in which the catalyst bed is positioned. The effect of reaction pressure is shown in FIG. 1.

It should be noted that the term "DIBK" includes both isomers in FIG. 1 (and in the other Figures). The diamond data points in FIG. 1 are collected at a reactor pressure of 552 kPa (80 psig). The triangle data points in FIG. 1 are collected at a reactor pressure of 138 kPa (20 psig). The data in FIG. 1 shows the significantly improved MIBK to DIBK ratio obtained using a reaction pressure of 552 kPa (80 psig) relative to the prior art reaction pressure of 138 kPa (20 psig) over a $C_3$ (DMK and IPA combined) conversion ranging from about 26 to about 38 weight percent.

Example 2

Preparation of Zirconium/Palladium on Alumina; Catalyst 1

24.95 g of G55B alumina (Sud Chemie) containing 0.05 wt % Pd is impregnated via incipient wetness with 10.13 g of $ZrOCl_2 \cdot 8H_2O$ dissolved in 15 ml deionized water. The resulting solid is dried for 1 hour at 25 degrees Celsius and then for 16 hours at 110 degrees Celsius (° C.). The solid pellets are calcined at 450° C. in air for 3.5 hr. The final loadings based on their oxides are Zr=13.5 wt % and Pd=0.044 wt %.

Condensation of DMK Using the Zirconium/Palladium on Alumina; Catalyst 1

The reactor is charged with 20 ml of the catalyst. The catalyst is reduced at 150° C. with a $N_2:H_2=2:1$ gas mixture at 75 ml/min for 1 hr, followed by $N_2:H_2=1:1$ at 100 ml/min for 1 hour, and then $H_2=50$ ml/min for 1 hour. The $H_2$ flow is reduced to 38 ml/min and acetone:$H_2O=97:3$ is fed at LHSV=1 $hr^{-1}$. The reaction temperature is varied between 100-150° C. by controlling the temperature of the furnace in which the catalyst bed is positioned in order to vary the conversion. The effect of reaction pressure is shown in FIG. 2, wherein DIBK includes both isomers.

Figure 2:
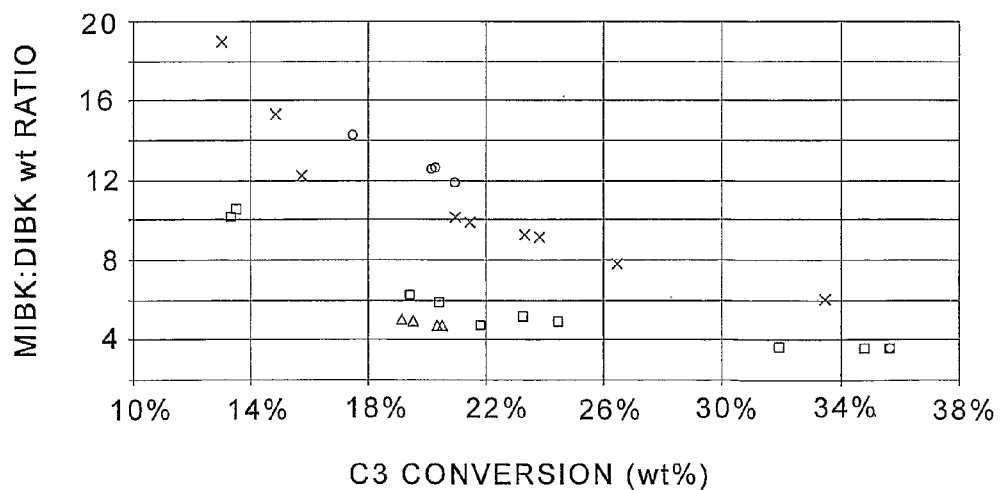

The circle data points in FIG. 2 are collected at a reactor pressure of 965 kPa (140 psig). The X data points in FIG. 2 are collected at a reactor pressure of 689 kPa (100 psig). The square data points in FIG. 2 are collected at a reactor pressure of 103-138 kPa (15-20 psig). The diamond data points in FIG. 2 are collected at a reactor pressure of 0 kPa (0 psig). The data in FIG. 2 shows the significantly improved MIBK to DIBK ratio obtained using the reaction pressures of the instant invention relative to the reaction pressures of the prior art over a $C_3$ conversion range from 12-36%.

Example 3

Preparation of Zirconium/Palladium on Alumina; Catalyst 2

25.02 g of CS350 alumina (Sud Chemie) is impregnated with a total of 7.31 g of $ZrOCl_2 \cdot 8H_2O$ in two steps in the following way. 5.34 g of $ZrOCl_2 \cdot 8H_2O$ in 5 ml deionized water is added to 25 gm of the alumina. The solid is rolled for one hour then placed in an oven at 105° C. for 16 hr. The recovered solid is impregnated with a second solution of 1.96 gm $ZrOCl_2 \cdot 8H_2O$ dissolved in 5 ml deionized water, rolled for 1 hour, and then dried at 105° C. for 4.5 hr. The recovered solid is calcined for 3.0 hr at 550° C. The calcined solid is impregnated with 0.23 ml of 10 wt % $Pd(NO_3)_2$ in 5 ml of deionized water, rolled for 1 hr and then dried overnight at 105° C. The solid is calcined at 550° C. for 3 hr. The final loadings based on their oxides are Zr=10 wt % and Pd=0.05 wt %.

Condensation of DMK Using the Zirconium/Palladium on Alumina; Catalyst 2

Figure 3:
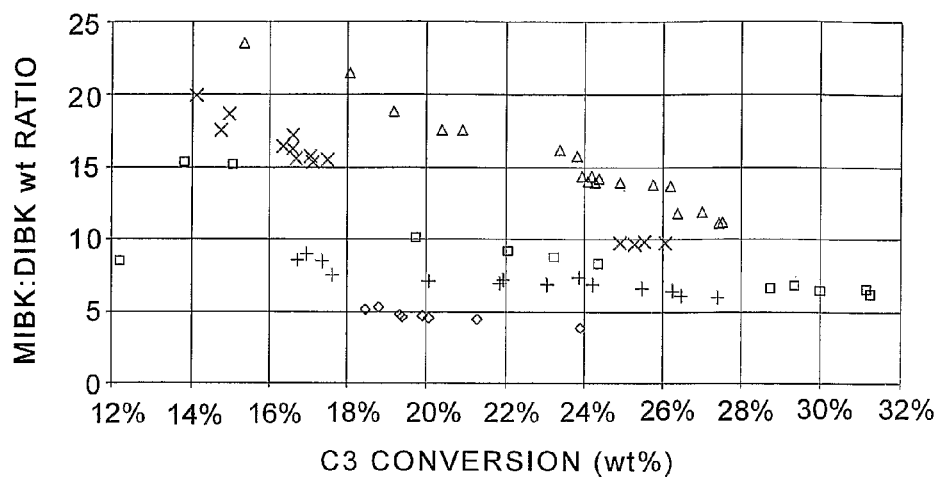

The reactor is charged with 20 ml of the catalyst. The catalyst is reduced at 150° C. with a $N_2:H_2=2:1$ gas mixture at 75 ml/min for 1 hr, followed by $N_2:H_2=1:1$ at 100 ml/min for 1 hour, and then $H_2=50$ ml/min for 1 hour. The $H_2$ flow is reduced to 38 ml/min and acetone:$H_2O=97:3$ was fed at LHSV=1 $hr^{-1}$. The reaction temperature is varied between 100-150° C. in order to vary the conversion. The results are shown in FIG. 3 for the pressure range of 0-2068 kPa (0-300 psig). The triangle data points in FIG. 3 are collected at a reactor pressure of 2068 kPa (300 psig). The X data points in FIG. 3 are collected at a reactor pressure of 1276-1379 kPa (185-200 psig). The square data points in FIG. 3 are collected at a reactor pressure of 689 kPa (100 psig). The +data points in FIG. 3 are collected at a reactor pressure of 345 kPa (50 psig). The diamond data points in FIG. 3 are collected at a reactor pressure of 0 kPa (0 psig). The data in FIG. 3 clearly show that the MIBK:DIBK ratio increases with increasing reactor pressure over a $C_3$ conversion range from 12-32%.

Example 4

Preparation of Zirconium Oxide/Copper/Chromium Catalyst 22.9 gm of $ZrO_2$ (⅛" pellets obtained from Degussa) is impregnated with 7.01 gm $Cu(NO_3)_2 \cdot 3H2O$ and 0.72 gm $Cr(NO_3)_3 \cdot 9H_2O$ dissolved in 4 ml of 70° C. deionized water.

The solid is rolled for one hour then dried overnight at 105° C. The solid is then calcined at 450° C. for 3 hours.

Condensation of Acetone/Isopropanol Using the Zirconium Oxide/Copper/Chromium Catalyst The reactor is charged with 14.4 ml of the catalyst. The catalyst is reduced at 150° C. with a $N_2:H_2=2:1$ gas mixture at 75 ml/min for 1 hr, followed by $N_2:H_2=1:1$ at 100 ml/min for 1 hour, and then $H_2=50$ ml/min for 1 hour. Gas flows are stopped and acetone:isopropanol:$H_2O$=52:40:8 is fed at LHSV=1 hr$^{-1}$. Experimental data are shown in FIG. 4.

Figure 4:
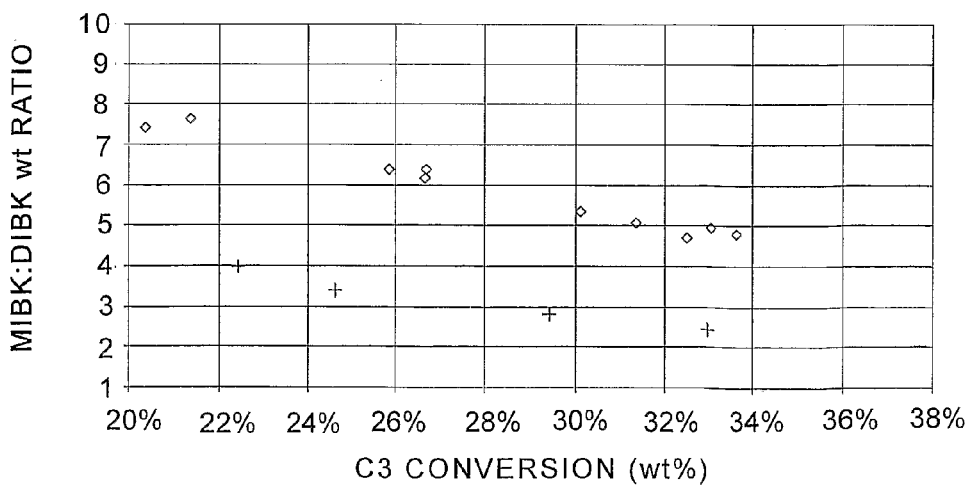

The diamond data points in FIG. 4 are collected at a reactor pressure of 241 kPa (35 psig). The + data points in FIG. 4 are collected at a reactor pressure of 0 kPa (0 psig). The data in FIG. 4 clearly show that the MIBK:DIBK ratio is better using a reactor pressure of the instant invention relative to a reactor pressure of the prior art over a $C_3$ conversion range from 22-38%.

Example 5

Condensation of Acetone/Isopropanol Using Copper/Chromium/Calciuym on Alumina Catalyst The reactor is charged with 20 ml of a Cu—Cr—Ca—$Al_2O_3$ catalyst with a nominal metal loading of Cu=10 wt %, Cr=0.4 wt %, and Ca=1.1 wt %. The catalyst is reduced at 150° C. with a $N_2:H_2=2:1$ gas mixture at 75 ml/min for 1 hr, followed by $N_2:H_2=1:1$ at 100 ml/min for 1 hour, and then $H_2=50$ ml/min for 1 hour. Gas flows are stopped and acetone:isopropanol:$H_2O$=52:40:8 is then fed at LHSV=1 hr$^{-1}$. Experimental data is shown in FIG. 5.

Figure 5:
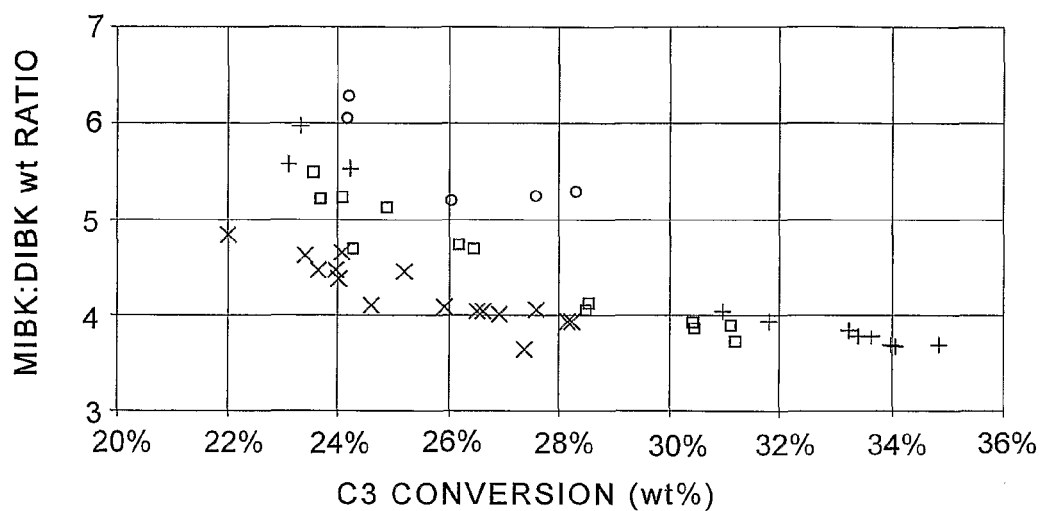

The circle data points in FIG. 5 are collected at a reactor pressure of 517 kPa (75 psig). The + data points in FIG. 5 are collected at a reactor pressure of 345 kPa (50 psig). The square data points in FIG. 5 are collected at a reactor pressure of 241 kPa (35 psig). The X data points in FIG. 5 are collected at a reactor pressure of 103 kPa (15 psig). The data in FIG. 5 clearly show that the MIBK:DIBK ratio increases with increasing reactor pressure over a $C_3$ conversion range from 22-35%.

CONCLUSION

While the instant invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

What is claimed is:

1. A method for the manufacture of MIBK and DIBK from DMK and/or IPA, and optionally water, by reacting, in the presence of a catalytic amount of an aldol condensation catalyst, a gaseous mixture comprising DMK and/or IPA, hydrogen and optionally water, at a reaction pressure of from greater than 30 psig up to 140 psig, wherein the catalyst comprises copper and chromium, to produce a reaction product, wherein the weight ratio of MIBK to DIBK in the reaction product is at least 4.

2. The method of claim 1, wherein the reaction pressure is greater than 31 psig.

3. The method of claim 1, wherein the reaction pressure is up to 100 psig.

4. The method of claim 1, wherein the reaction pressure is up to 100 psig.

5. The method of claim 1, wherein the reacting is conducted at a temperature of from 80 to 300 degrees Celsius.

6. The method of claim 1 wherein the manufacture of MIBK and DIBK is from a feed stream consisting essentially of IPA.

7. A method for the manufacture of MIBK and DIBK by reacting, in the presence of an aldol condensation catalyst, a gaseous mixture consisting essentially of DMK and/or IPA, hydrogen and optionally water, characterized by a reaction pressure of from greater than 30 psig up to 140 psig, wherein the catalyst comprises copper and chromium, to produce a reaction product, wherein the weight ratio of MIBK to DIBK in the reaction product is at least 4.

* * * * *